(12) United States Patent
Noguchi et al.

(10) Patent No.: US 8,551,410 B2
(45) Date of Patent: Oct. 8, 2013

(54) PHOTOPOLYMERIZATION DEVICE

(75) Inventors: Yukie Noguchi, Tokyo (JP); Kazuhisa Kashiwabara, Tokyo (JP)

(73) Assignee: GC Corporation, Tokyo (JP)

( * ) Notice: Subject to any disclaimer, the term of this patent is extended or adjusted under 35 U.S.C. 154(b) by 53 days.

(21) Appl. No.: 13/192,868

(22) Filed: Jul. 28, 2011

(65) Prior Publication Data

US 2012/0032575 A1 Feb. 9, 2012

(30) Foreign Application Priority Data

Aug. 9, 2010 (JP) ................................. 2010-178586

(51) Int. Cl.
*B01J 19/08* (2006.01)

(52) U.S. Cl.
USPC ........................... 422/131; 313/46; 250/492.1

(58) Field of Classification Search
USPC ............ 250/492.1; 313/46; 315/330; 522/33; 422/131

See application file for complete search history.

(56) References Cited

U.S. PATENT DOCUMENTS

2004/0051482 A1* 3/2004 Fregoso ..................... 315/291

FOREIGN PATENT DOCUMENTS

| JP | 2003-033374 A | 2/2003 |
| JP | 2005-161002 A | 6/2005 |

* cited by examiner

*Primary Examiner* — Anh Mai
*Assistant Examiner* — Brenitra M Lee
(74) *Attorney, Agent, or Firm* — Ladas & Parry LLP

(57) ABSTRACT

The present invention provides a photopolymerization device which allows a space irradiated with a light to have a high temperature while inhibiting a temperature rise of a light source used for the space. The photopolymerization device comprises: a housing; a polymerization space which is surrounded by a wall in the housing and in which polymerization is carried out; a light-emitting diode light source which irradiates a light for polymerization into the polymerization space; and a temperature control device which heats inside the polymerization space, wherein the light-emitting diode light source is arranged outside the polymerization space.

7 Claims, 2 Drawing Sheets

PHOTOPOLYMERIZATION DEVICE

TECHNICAL FIELD

The present invention relates to a photopolymerization device which hardens a light hardening material (generally called light curing material) used for a dental prosthesis in a dental field, particularly in a dental technical field.

BACKGROUND ART

In a dental field, particularly in a dental technical field, when making a dental prosthesis such as a restorative substance for a tooth and an artificial tooth, a method to form a shape by using a light hardening material before the light hardening material is hardened and to fix the shape by irradiating a light to harden the shape is widely employed. Here, a device which irradiates a light to harden (polymerize) a light hardening material is a photopolymerization device.

Conventionally, a fluorescent lamp, halogen lamp, xenon lamp, and the like are used as a light source of a photopolymerization device. However, these light sources do not necessarily have long life; thus it is necessary to change the light sources quite frequently. Further, the above light sources irradiate a light with a wide wavelength range, so they include a wavelength outside a wavelength range necessary to harden a light hardening material and use an energy for an unnecessary wavelength range; therefore effective irradiation of light cannot be expected.

On the other hand, however, in a case of irradiating a light by using a halogen lamp or xenon lamp, the light source itself becomes a heat source, and thus hardening (polymerizing) by light and hardening (polymerizing) by a heat can be carried out simultaneously; in this respect, despite the cost for replacement due to life expiration, a halogen lamp and a xenon lamp have been used as an importance light source.

With regard to this, Patent Documents 1 and 2 disclose a photopolymerization device which uses a blue light-emitting diode. According to these patent documents, a wavelength which is capable of hardening (polymerizing) a number of commercially available dental light hardening materials matches a wavelength of a blue light-emitting diode. Accordingly, it is possible to provide a photopolymerization device which hardens a light hardening material with a smaller amount of energy than an amount of energy necessitated by a conventional light source, and which does not require frequent replacement of a light source because of a long-life property of a light-emitting diode.

Further, according to a polymerization device disclosed in Patent Document 2, it is possible to set a condition which is suitable for a hardening property of a light hardening material by further providing a heating device to the polymerization device.

CITATION LIST

Patent Documents

Patent Document 1: Japanese Patent Application Laid-Open (JP-A) No. 2003-033374
Patent Document 2: JP-A No. 2005-161002

SUMMARY OF THE INVENTION

Problems to be Solved by the Invention

However, there is a case that with a photopolymerization device disclosed in Patent Document 1, it is not possible to raise the temperature of a light hardening material sufficiently, and that although the light hardening material gets hardened, the hardness (intensity) thereof cannot be ensured. Further, there is a possibility that with a photopolymerization device disclosed in Patent Document 2, an inner area of the device is heated up, which is caused by heating with a heating device; thereby, in combination with a heat of a blue light-emitting diode, the temperature in the device exceeds the temperature which is permissible to the blue light-emitting diode.

Accordingly, in view of the above described problems, the present invention provides a photopolymerization device which allows a space irradiated with a light to have a high temperature while inhibiting a temperature rise of a light source used for the space.

Means for Solving the Problems

Hereinafter, the present invention will be described.

A first aspect of the present invention is a photopolymerization device comprising: a housing; a polymerization space which is surrounded by a wall in the housing and in which polymerization is carried out; a light-emitting diode light source which irradiates a light for polymerization into the polymerization space; and a temperature control device which heats inside the polymerization space, wherein the light-emitting diode light source is arranged outside the polymerization space.

A second aspect of the invention is the photopolymerization device according to the first aspect, wherein at least a part of a wall forming the polymerization space is formed of a translucent (or transparent) member, and a light from the light-emitting diode light source transmitted through the translucent member irradiates the polymerization space.

A third aspect of the invention is the photopolymerization device according to the first aspect, wherein the light-emitting diode light source is provided with a heat dissipating device.

A fourth aspect of the present invention is a photopolymerization device comprising: a housing; a polymerization space which is surrounded by a wall in the housing and in which polymerization is carried out; a light-emitting diode light source which irradiates a light for polymerization into the polymerization space; and a temperature control device which heats inside the polymerization space, wherein the light-emitting diode light source is arranged outside the polymerization space; the temperature control device comprises a cooling device which cools the light-emitting diode light source, and a heat supply device which supplies the polymerization space with a heat generated from the light-emitting diode light source through the cooling device; and the polymerization space is heated by the heat generated from the light-emitting diode light source.

A fifth aspect of the present invention is the photopolymerization device according to the fourth aspect, wherein at least a part of a wall forming the polymerization space is formed of a translucent member, and a light from the light-emitting diode light source transmitted through the translucent member irradiates the polymerization space.

A sixth aspect of the present invention is the photopolymerization device according to the fourth aspect, wherein the cooling device is provided with a Peltier device, the light-emitting diode light source is arranged on an endothermic side of the Peltier device, directly or indirectly through other members, and a heat from an exothermic side of the Peltier device is supplied to the polymerization space.

A seventh aspect of the present invention is the photopolymerization device according to the fourth aspect, wherein the cooling device and the heat supply device are respectively provided with a heat sink, and a heat generated from the light-emitting diode light source is supplied to the polymerization space through the heat sink.

An eighth aspect of the present invention is the photopolymerization device according to fourth aspect, further comprising other heating devices which are capable of heating inside the polymerization space.

Effects of the Invention

With the present invention, it is possible to harden a light hardening material used for a dental prosthesis and the like by using a light-emitting diode light source, and to increase the hardness (intensity) of the light hardening material by raising the temperature inside a space irradiated with a light (polymerization space). Even when the temperature inside the polymerization space is raised, the temperature of the light-emitting diode light source can be kept within a permissible temperature range.

DESCRIPTION OF MODES FOR CARRYING OUT THE INVENTION

The functions and benefits of the present invention described above will be apparent from the following modes for carrying out the invention. However, the invention is not limited to the embodiment.

Figure 1:
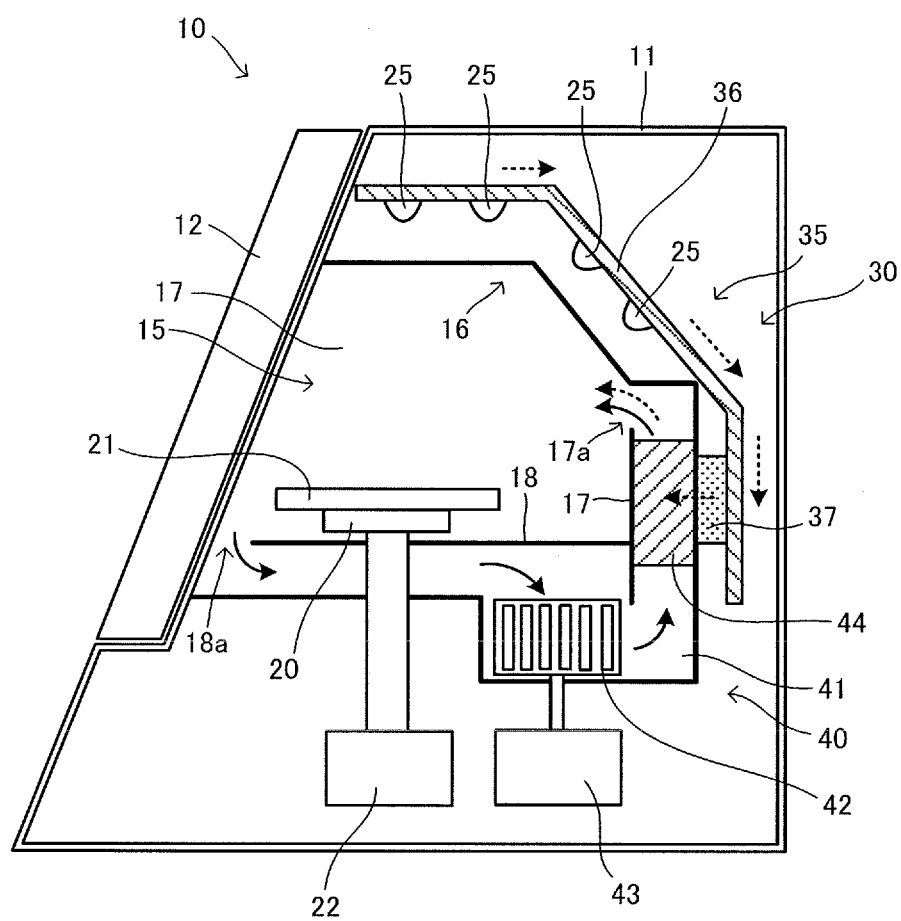
FIG. 1 is a vertically cross-sectional view conceptually showing a configuration of a photopolymerization device according to one embodiment.

FIG. 1 is a vertically cross-sectional view conceptually showing a configuration of a photopolymerization device 10 according to one embodiment.

The photopolymerization device 10 comprises: a body 11; a lid 12; a polymerization space 15; a table 20; a light source 25; and a temperature control device 30.

As seen from FIG. 1, the body 11 functions as a housing and becomes a base configuration for the photopolymerization device; and a majority of each of the members composing the photopolymerization device 10 are arranged inside the body 11.

The lid 12 functions as a part of a wall forming the polymerization space 15 and is a lid member which is arranged in a manner covering an opening provided to the body 11. The lid 12 is openable and closable: at the time of opening, it is possible to lead to the polymerization space 15 from outside, and at the time of closing, the polymerization space 15 is closed. In other words, it is possible to put a dental prosthesis and the like into the polymerization space 15 and take a dental prosthesis and the like out of the polymerization space 15 by opening the lid 12. With the lid 12 closed, a light irradiates a dental prosthesis and the like.

The polymerization space 15 is a space configured to be inside the body 11. A dental prosthesis and the like are put in the space and the space is irradiated with a light. The polymerization space 15 is configured to be surrounded by an upper wall 16; a side wall 17; a bottom wall 18; and the lid 12 when the polymerization space 15 is closed.

Here, the upper wall 16 is composed of a translucent member so that a light from the light source 25 can be transmitted.

A member composing the upper wall 16 is not particularly restricted as long as it is a translucent member. For the purpose of diffusing or collecting more light from the light source, a lens may be provided to the upper wall 16. The translucent member may have two layers of materials, the material on a side of the polymerization space 15 and the material on an outer side of the polymerization space 15 being different from each other. Examples of the materials include a transparent vinyl chloride member laminating a transparent polymide film on the side of the polymerization space 15; and a glass lens laminating a transparent acrylic sheet on the side of the polymerization space 15. With this configuration, even when a member on a side exposed to inside of the polymerization space 15, among the translucent members, is stained by a material to be hardened, it is possible to replace only a layer on the side of the polymerization space 15; thereby, it is possible to prevent attenuation of an amount of light.

Further, the side wall 17 and the bottom wall 18 are respectively provided with an inlet hole 17a, and an outlet hole 18a which communicate with a ventilation flue 41 of the below-described temperature control device 30.

The table 20 is a table-like member which is arranged at the bottom of the polymerization space 15 and which can be rotated by a motor 22. An attachment 21 is disposed on the table 20, and a dental prosthesis and the like are placed on the attachment 21. Since the table 20 can be rotated by the motor 22, it is possible to rotate the attachment 21 disposed on the table 20 and the dental prosthesis and the like as well; thereby more uniform polymerization becomes possible.

Here, the attachment 21 is preferably detachable from the table 20. Further, it is preferable that several types of the attachments 21 in different height be prepared and that the attachments can be selected so that a light can be adequately irradiated according to the size of a dental prosthesis and the like. By this, it is possible to handle a number of different types of dental prosthesis and the like.

The light source 25 is a light-emitting diode which emits a light including a wavelength necessary for hardening a light hardening material used for a dental prosthesis and the like. Usually, a wavelength region in which this kind of light hardening material is hardened is 360 nm to 500 nm, and thus a blue or white light-emitting diode is preferable. The hardness (intensity) of this kind of light hardening material such as this is increased when the temperature is approximately 80° C. to 120° C. at the time of hardening.

Prototypical examples of a light hardening material include a photo-radical polymerizing material such as camphorquinone. A wavelength for the light hardening material to start to become polymerized is approximately 460 nm.

A diode used as a light source is not particularly restricted as long as it includes a wavelength which allows a light hardening material to start to become hardened. A blue light-emitting diode usually includes a wavelength such as this, and thus can be preferably applied.

On the other hand, in a white light emitting diode, there are a type in which a white light is obtained by using a fluorescent body, and a type in which a white light is obtained by an light emitting device in light's three primary colors: red, green, and blue; however, the latter is preferable since the intensity of a wavelength for hardening a light hardening material is higher.

In this embodiment, the light source 25 is arranged on a upper side of the photopolymerization space 15, and a light from the light source is irradiated to the photopolymerization space 15 through the translucent upper wall 16. In this way, the light source 25 is not disposed directly inside the photopolymerization space 15. With this configuration, even when an space inside the photopolymerization space 15 is heated, the light source 25 is not heated, and is protected from the heat.

Further, in this embodiment, the four light sources 25 are arranged on an upper portion. However, the arrangement of the light sources is not restricted to this; the further adequate number of light sources and a further adequate arrangement of light sources depending on the difference in the types of irradiated objects can be applied. For example, a part of the side wall 17 may also be composed of a translucent material and may arrange the light source outside the side wall 17.

The temperature control device 30 is a device to raise the temperature in the photopolymerization space 15 by using a heat from the light source 25. With this device, it is possible to raise the temperature in the photopolymerization space 15 efficiently, and even then, the light source 25 is kept within a permissible temperature range. In other words, it is possible to set temperature conditions under which to increase the hardness (intensity) of a light hardening material, while keeping the light source in an appropriate state. Details are as follows.

As seen from FIG. 1, the temperature control device 30 is provided inside the body 11 and comprises a cooling device 35, a heat supply device 40, and a control device (not shown).

The cooling device 35 is a device which has a function to transfer a heat from the light source 25 to the heat supply device 40, and which comprises a heat sink 36 and a Peltier device 37.

The heat sink 36 is arranged in a manner contacting with the light source 25, and absorbs a heat generated in the light source 25 to diffuse the heat. Accordingly, the heat sink 36 is composed of a material with high heat conductivity, and examples of the material include copper and aluminum.

The Peltier device 37 is a device which has a Peltier effect, and by running an electric current, one side of the Peltier device 37 absorbs a heat and the other the Peltier device 37 emits a heat based on the heat absorbed. The Peltier device 37 is arranged in a manner that the endothermic side of the Peltier device 37 contacts with the heat sink 36. Accordingly, the exothermic side of the Peltier device 37 is on the opposite side of the endothermic side. In other words, the Peltier device 37 absorbs a heat generated from the light source through the heat sink 36.

The heat supply device 40 is a device to supply a heat received from the cooling device 35 to the polymerization space 15, and comprises a ventilation flue 41, an air blower 42, and a heat sink 44.

The ventilation flue 41 is a flow path which enables the air to pass through. As seen from FIG. 1, one end of the ventilation flue 41 leads to the outlet hole 18a of the bottom wall 18 in the polymerization space 15, whereas the other end of ventilation flue 41 leads the inlet hole 17a of the side wall 17.

The air blower 42 is arranged inside the ventilation flue 41, and is a device which functions as a power source for transferring the air in the ventilation flue 41. Here, a conventional air blower such as a fan can be applied and this is driven by a motor 43.

The heat sink 44 is a heat sink a part of which is arranged inside the ventilation flue 41 and another part of which is arranged in a manner contacting the exothermic side of the above described Peltier device 37. Therefore, it is possible to absorb a heat of the Peltier 37 by the heat sink 44 and to supply the heat into the air blower 41.

The control device is a device to activate and stop the air blower 42, and turn on and off the light source 25 as needed, while knowing a thermal state in the polymerization space 15. Here, the thermal state in the polymerization space 15 can be known by utilizing a temperature measuring sensor (a thermocouple, temperature measuring resistance body, or the like). Based on the information from the temperature measuring sensor, the control device makes judgments, under a prescribed condition, to turn off the light source 25 and to stop the air blower 42 in case that lowering the temperature is necessary. On the other hand, in case that raising the temperature is necessary, the control device can give directions to continue to turn on the light source 25 and continue to operate the air blower 42.

Accordingly, a control device as above may comprise an input port in which temperature information and the like are inputted; a read-only memory (ROM) in which information on conditions for judgment and the like are recorded in advance; a central processing unit (CPU) for carrying out an operation based on the inputted information; a random access memory (RAM) which functions as a work area for the operation and as a temporary memory; and an output port for outputting the result of the operation.

The control device may further comprise a device to measure and control an amount of light. CCD, for example, is disposed as a sensor for measuring an amount of light; and thereby monitoring is performed to secure the amount of light needed to polymerize (harden) a light hardening material and the like.

With the photopolymerization device 10 comprising the constituent members as above, it is possible to form a dental prosthesis and the like, for example in the following ways.

A dental prosthesis and the like formed of a light hardening material which has not become hardened is placed on the attachment 21 of the body 11. Next, a polymerization space 15 is formed by closing the lid 12 and the light source is turned on; at the same time as this, the temperature control device 30 is operated as well. Then, the light hardening material for the dental prosthesis and the like first starts to be polymerized (hardened) by a light from the light source 25. On the other hand, as shown by a dotted arrow in FIG. 1, a heat generated from the light source 25 is absorbed into the Peltier device 37 through the heat sink 36, and the heat sink 44 is heated by the heat.

Further, as shown by a solid arrow in FIG. 1, by operating the air blower 42, the air flows from the outlet hole 18a to the inlet hole 17a. Here, the heated heat sink 44 heats the air flowing inside the ventilation flue 41. The heated air flows into the polymerization space 15 from the inlet hole 17a by the airflow from the air blower 42. Because of this, the polymerization space 15, or the light hardening material for the dental prosthesis and the like is warmed. In general, the hardness (intensity) of a light hardening material is increased when the temperature is approximately 80° C. to 120° C. at the time of hardening. Therefore, with the photopolymerization device 10, it is possible to obtain a high level of hardness (intensity) in the dental prosthesis and the like after being formed. At this point, the polymerization space 15 is heated as described above; however since the light source 25 is isolated from the polymerization space 15, and also is cooled by the cooling device 35, an appropriate operation of the light source 25 is ensured.

Here, the control device obtains the temperature of the polymerization space 15, and controls the temperature so that the temperature is kept within an adequate temperature range. Specifically, when the temperature of the polymerization space 15 is raised to a predetermined temperature or above, the light source 25 and the air blower 42 are stopped; thereby the temperature of the polymerization space 15 can be lowered. On the other hand, when the polymerization space 15 does not reach a predetermined temperature, the light source 25 continues to be turned on and the air blower 42 continues to be operated.

As described above, with the photopolymerization device 10, while it is possible to raise the temperature in the polymerization space 15, it is also possible to keep the temperature in the light source 25 within a permissible temperature range. Moreover, since a heat which heats the polymerization space 15 utilizes a heat released from the light source 25, the photopolymerization device 10 with an efficient energy is made possible.

The photopolymerization device 10 may arrange other heating devices in the polymerization space 15 as a supplementary. The heating device can help overcome the situation when a sufficient temperature cannot be obtained in the polymerization space 15 by only a heat released from the light source 25. Examples of other heating devices include an appliance such as an infrared heater and a ceramic heater, and a halogen lamp and xenon lamp which can be used as a light source.

In addition, in this embodiment, the cooling device 35 is provided with the Peltier device 37, thereby efficiently utilizing a released heat; however, it is possible to arrange the heat sink 26 of the cooling device 35 and the heat sink 44 of the heat supply device 40 in a manner being directly contacted with each other, without having the Peltier device 37. With this configuration as well, it is possible to supply a heat generated in a light source to the polymerization space.

Figure 2:
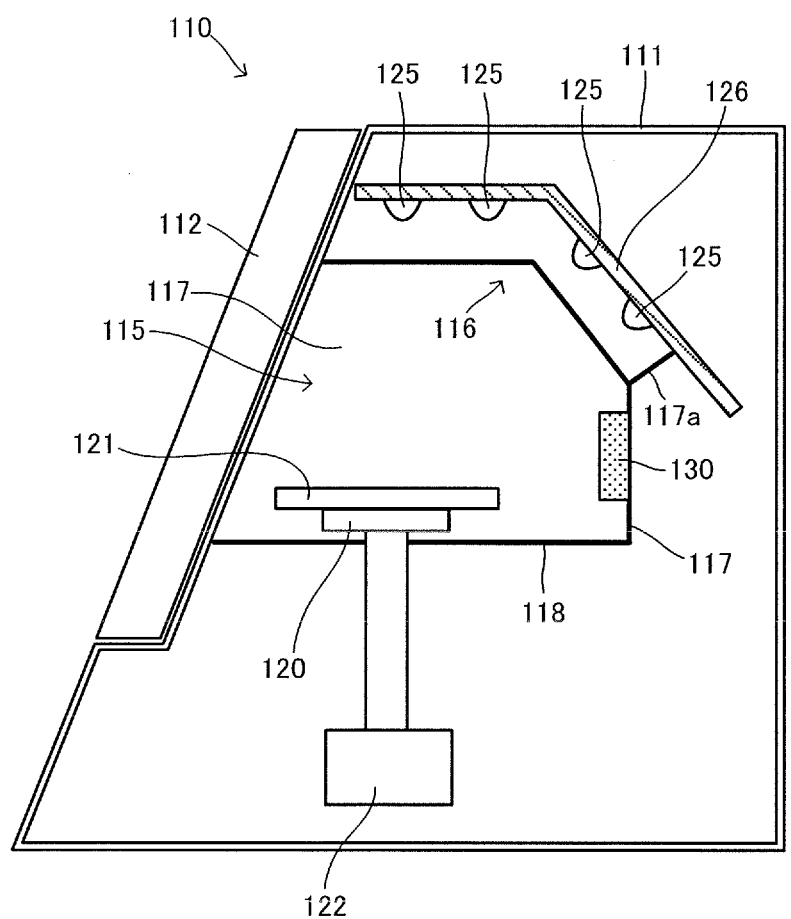
FIG. 2 is a vertically cross-sectional view conceptually showing a configuration of a photopolymerization device according to another embodiment.

FIG. 2 is a vertically cross-sectional view conceptually showing a configuration of a photopolymerization device 110 according to another embodiment.

The photopolymerization device 110 comprises: a body 111; a lid 112; a polymerization space 115; a table 120; a light source 125; a heat dissipating device 126; and a temperature control device 130.

As seen from FIG. 2, the body 111 functions as a housing and becomes a base configuration for the photopolymerization device 110; and a majority of each of the members composing the photopolymerization device 110 are arranged inside the body 111. The body 111 may be provided with a hole communicating inside with outside, and the hole may be provided with an air blower such as a fan. With this configuration, it is possible to adjust the temperature inside the body 111, and to efficiently dissipate a heat of the below described light source 125.

A lid 112 functions as a part of a wall forming the polymerization space 115 and is a lid member which is arranged in a manner covering an opening provided to the body 111. The lid 112 is openable and closable: at the time of opening, the polymerization space 115 can be led to from outside, and at the time of closing, the polymerization space 115 is closed. In other words, it is possible to put a dental prosthesis and the like in the polymerization space 115 and take a dental prosthesis and the like out of the polymerization space 115 by opening the lid 112. With the lid 112 closed, a light irradiates a dental prosthesis and the like.

The polymerization space 115 is a space configured to be inside the body 111. A dental prosthesis and the like are put in the space and the space is irradiated with a light. The polymerization space 115 is configured to be surrounded by an upper wall 116; a side wall 117; a bottom wall 118; and also the lid 112 when the polymerization space 115 is closed.

Here, the upper wall 116 is composed of a translucent member so that a light from the light source 125 can be transmitted. A member composing the upper wall 116 is not particularly restricted as long as it is a translucent member. For the purpose of diffusing or collecting more light from the light source, a lens may be provided to the upper wall 116. The translucent member may have two layers of materials, the material on a side of the polymerization space 115 and the material on an outer side of the polymerization space 115 being different from each other. Examples of the materials include a transparent vinyl chloride member laminating a transparent polymide film on the side of the polymerization space 115; and a glass lens laminating a transparent acrylic sheet on the side of the polymerization space 115. With this configuration, even when a member on a side exposed to inside of the polymerization space 115, among the translucent members, is stained by a material to be hardened, it is possible to replace only the layer on the side of the polymerization space 115; thereby, it is possible to prevent attenuation of an amount of light.

Here, as seen from FIG. 2, a wall 117a can be vertically arranged in a manner facing from an outer side surface of the polymerization space 115 toward the light source 125 and the heat dissipating device 126. With this, it is possible to block off the influx of a heat from the polymerization space 115 and the temperature control device 130 into a side of the light source 125, and further possible to inhibit these heat influences.

Descriptions of a table 120, a motor 122, and an attachment 121 will be omitted since the descriptions are the same as those of the table 20, the motor 22, and the attachment 21.

Descriptions of a light source 125 will also be omitted since the descriptions are the same as those of the light source 25.

The light source 125 is arranged on a upper side of the photopolymerization space 115, and a light from the light source is irradiated to the photopolymerization space 115 through the translucent upper wall 116. In this way, the light source 125 is not disposed directly inside the photopolymerization space 115. With this configuration, even when a space inside the photopolymerization space 115 is heated, the light source 125 is not heated, and is protected from the heat.

Further, in this embodiment, the four light sources 125 are arranged on an upper portion. However, the arrangement of the light sources is not restricted to this; the further adequate number of light sources and a further adequate arrangement of light sources depending on the difference in the types of irradiated objects can be applied. For example, a part of the side wall 117 may also be composed of a translucent material and may arrange a light source 125 outside the side wall 117.

The heat dissipating device 126 is a device to dissipate a heat generated from the light source 125. In this embodiment, a heat sink 126 is arranged as the heat dissipating device 126. The heat sink 126 is arranged in a manner contacting with the light source 125, and absorbs a heat generated in the light source 125 to diffuse the heat. Accordingly, the heat sink 126 is composed of a material with high heat conductivity, and examples include copper and aluminum. The diffused heat is released into the air. By this, the light source 125 is kept within a permissible temperature range, and thus the reliability of the operation is enhanced.

As described above, if the housing 111 is provided with a hole or an air blower, efficient heat dissipation can be further achieved.

The temperature control device 130 is arranged in the polymerization space 115 and is a device to raise the temperature in the polymerization space 115. Specifically, examples include an appliance which emits heat by providing electricity, such as an infrared heater and a ceramic heater; an electron beam irradiation appliance used for a microwave oven and the like; and a halogen lamp and xenon lamp, which can also be used as a light source.

With the photopolymerization device 110, even when the temperature in the polymerization space 115 is raised, the temperature in the light source 125 can be kept within a permissible temperature range. In other words, it is possible to set temperature conditions under which to increase hardness (intensity) of a light hardening material, while keeping the light source in an appropriate state.

The temperature control device 130 may comprise a control device not shown in a figure. The control device is a device to activate and stop the temperature control device 130, as needed, while knowing a thermal state in the polymerization space 115. Here, the thermal state in the polymerization space 115 can be known by utilizing a temperature measuring sensor (a thermocouple, temperature measuring resistance body, or the like). Based on the information from the temperature measuring sensor, the control device makes judgments, under a prescribed condition, to stop the temperature control device 130 in case when lowering the temperature is necessary. On the other hand, in case when raising the temperature is necessary, the control device can give a direction to operate the temperature control device 130.

Accordingly, a control device as above may comprise an input port in which temperature information and the like are inputted; a read-only memory (ROM) in which information on conditions for judgment and the like are recorded; a central processing unit (CPU) for carrying out an operation based on the inputted information; a random access memory (RAM) which functions as a work area for the operation and as a temporary memory; and an output port for outputting the result of the operation.

The control device may further comprise a device to measure and control an amount of light. CCD, for example, is arranged as a sensor for measuring an amount of light; thereby monitoring is performed to secure the amount of light needed to polymerize (harden) a light hardening material and the like.

With the photopolymerization device 110 comprising the constituent members as above, it is possible to form a dental prosthesis and the like, for example in the following ways.

A dental prosthesis and the like formed of a light hardening material which has not become hardened is placed on the attachment 121. Next, a polymerization space 115 is formed by closing the lid 112 and the light source 125 is turned on; at the same time as this, the temperature control device 130 is operated as well. Then, the light hardening material for the dental prosthesis and the like first starts to be polymerized (hardened) by a light from the light source 125. On the other hand, the polymerization space 115, or the light hardening material for the dental prosthesis and the like is warmed by a heat generated from the temperature control device 130. In general, the hardness (intensity) of a light hardening material is increased when the temperature is approximately 80° C. to 120° C. at the time of hardening. Therefore, with the photopolymerization device 110, it is possible to obtain a high level of hardness (intensity) in the dental prosthesis and the like after being formed. At this point, the polymerization space 115 is heated as described above; however, since the light source 125 is isolated from the polymerization space 115, an appropriate operation of the light source 125 is ensured without being influenced by the heat.

Here, the control device obtains the temperature of the polymerization space, and control the temperature so that the temperature is kept within an adequate temperature range. Specifically, when the temperature of the polymerization space 115 is raised to a predetermined temperature or above, the temperature control device 130 is stopped; thereby the temperature of the polymerization space 115 can be lowered.

On the other hand, when the polymerization space 115 does not reach a predetermined temperature, the temperature control device 130 continues to be operated.

As described above, with the photopolymerization device 110, while it is possible to raise the temperature in the polymerization space 115, it is also possible to keep the temperature in the light source 125 within a permissible temperature range.

The invention has been explained above as to the embodiment which is supposed to be practical as well as preferable at present. However, it should be understood that the invention is not limited to the embodiment disclosed in the specification and can be appropriately modified within the range that does not depart from the gist or spirit of the invention, which can be read from the appended claims and the overall specification, and a photopolymerization device with such modifications is also encompassed within the technical range of the invention.

DESCRIPTION OF THE REFERENCE NUMERALS 10 photopolymerization device
11 body (housing)
12 lid
15 polymerization space
16 upper wall
17 side wall
18 bottom wall
20 table
21 attachment
22 motor
25 light source
30 temperature control device
35 cooling device
36 heat sink
37 Peltier device
40 heat supply device
41 ventilation flue
42 air blower
43 motor
44 heat sink
110 photopolymerization device
111 body (housing)
112 lid
115 polymerization space
120 table
125 light source
126 heat dissipating device
130 temperature control device

The invention claimed is:
1. A photopolymerization device comprising:
a housing;
a polymerization space which is surrounded by a wall in the housing and in which polymerization is carried out;
a light emitting diode light source which irradiates a light for polymerization into the polymerization space; and
a temperature control device which heats inside the polymerization space, wherein the whole body of the light emitting diode light source is arranged outside the wall forming the polymerization space;
at least a part of the wall forming the polymerization space is formed of a transparent or translucent member; and
a light from the light emitting diode light source transmitted through the transparent or translucent member irradiates the polymerization space.

2. The photopolymerization device according to claim 1, wherein the light emitting diode light source is provided with a heat dissipating device.

3. A photopolymerization device comprising:
a housing;
a polymerization space which is surrounded by a wall in the housing and in which polymerization is carried out;
a light emitting diode light source which irradiates a light for polymerization into the polymerization space; and
a temperature control device which heats inside the polymerization space, wherein the light emitting diode light source is arranged outside the polymerization space;
the temperature control device comprises a cooling device which cools the light emitting diode light source, and a heat supply device which supplies the polymerization space with a heat generated from the light emitting diode light source through the cooling device; and
the polymerization space is heated by the heat generated from the light emitting diode light source.

4. The photopolymerization device according to claim 3, wherein at least a part of a wall forming the polymerization space is formed of a transparent or translucent member, and a light from the light emitting diode light source transmitted through the transparent or translucent member irradiates the polymerization space.

5. The photopolymerization device according to claim 3, wherein the cooling device is provided with a Peltier device, the light emitting diode light source is arranged on an endothermic side of the Peltier device directly or indirectly through other members, and a heat from an exothermic side of the Peltier device is supplied to the polymerization space.

6. The photopolymerization device according to claim 3, wherein the cooling device and the heat supply device are respectively provided with a heat sink, and a heat generated from the light emitting diode light source is supplied to the polymerization space through the heat sink.

7. The photopolymerization device according to claim 3, further comprising other heating devices which are capable of heating inside the polymerization space.

\* \* \* \* \*